(12) United States Patent
Akerson et al.

(10) Patent No.: US 10,231,491 B2
(45) Date of Patent: Mar. 19, 2019

(54) MULTI-LAYER NURSING GARMENT

(71) Applicants: Deeanne Akerson, Oceanside, CA (US); Garret Akerson, Oceanside, CA (US)

(72) Inventors: Deeanne Akerson, Oceanside, CA (US); Garret Akerson, Oceanside, CA (US)

(*) Notice: Subject to any disclaimer, the term of this patent is extended or adjusted under 35 U.S.C. 154(b) by 0 days.

(21) Appl. No.: 15/694,995

(22) Filed: Sep. 4, 2017

(65) Prior Publication Data

US 2018/0064178 A1   Mar. 8, 2018

Related U.S. Application Data

(60) Provisional application No. 62/383,457, filed on Sep. 4, 2016.

(51) Int. Cl.
| | |
|---|---|
| *A41C 3/04* | (2006.01) |
| *A41C 3/12* | (2006.01) |
| *A61B 5/00* | (2006.01) |
| *G04F 10/00* | (2006.01) |
| *A41C 3/00* | (2006.01) |

(52) U.S. Cl.
CPC .............. *A41C 3/04* (2013.01); *A41C 3/0021* (2013.01); *A41C 3/12* (2013.01); *A61B 5/0024* (2013.01); *A61B 5/4288* (2013.01); *A61B 5/6804* (2013.01); *A61B 5/7282* (2013.01); *G04F 10/00* (2013.01)

(58) Field of Classification Search
CPC ....................................................... A41C 3/04
See application file for complete search history.

(56) References Cited

U.S. PATENT DOCUMENTS

| | | | | |
|---|---|---|---|---|
| 4,335,728 | A * | 6/1982 | Fildan ...................... | A41C 3/04 450/36 |
| 5,624,296 | A * | 4/1997 | Weber-Unger .......... | A41C 3/04 2/101 |
| 6,083,079 | A * | 7/2000 | Pearson ................... | A41C 3/00 450/1 |
| 6,165,047 | A | 12/2000 | Scott et al. | |
| 6,227,936 | B1 * | 5/2001 | Mendoza ................. | A41C 3/04 2/104 |
| 6,364,739 | B1 * | 4/2002 | Dutka ...................... | A41C 3/04 450/36 |
| 6,645,041 | B2 * | 11/2003 | Sørensen ................. | A41C 3/04 2/104 |
| 7,094,217 | B2 | 8/2006 | Fialkoff | |
| 8,057,452 | B2 | 11/2011 | Fialkoff | |
| 8,192,247 | B2 | 6/2012 | Abbaszadeh | |

(Continued)

*Primary Examiner* — Gloria M Hale
(74) *Attorney, Agent, or Firm* — Eric Hanscom

(57) ABSTRACT

The present invention teaches a multi-layered nursing garment. The multi-layered nursing garment includes breasts support having a pair of breast cups, shoulder straps and a chest band. Each breast cup is comprised of two or more layers. Further a clasp for attaching an outer removable layer with a shoulder strap and a clip is configured for attaching another, inner layer. The invention provides a number of combinations of clips, clasps, and layers but which a breastfeeding woman can selectively open the nursing garment to accomplish breastfeeding and/or milk pumping from either breast, and has the capacity to engage in said events simultaneously.

20 Claims, 8 Drawing Sheets

(56) References Cited

U.S. PATENT DOCUMENTS

| | | |
|---|---|---|
| 8,307,463 B2 | 11/2012 | Ritchie |
| 8,469,770 B2 | 6/2013 | Alva |
| 8,657,643 B2 | 2/2014 | Perez |
| 9,155,339 B2 | 10/2015 | Alva |
| 9,167,855 B2 | 10/2015 | Abbaszadeh |
| 9,402,425 B2 | 8/2016 | Cortese et al. |
| 9,498,005 B2 | 11/2016 | Abbaszadeh |
| 9,629,396 B2 | 4/2017 | Alva |
| 9,872,524 B2 | 1/2018 | Abbaszadeh |
| 9,894,942 B2 | 2/2018 | Burrell |
| 2005/0085160 A1* | 4/2005 | Johnstone ............... A41C 3/04 450/36 |
| 2008/0003921 A1* | 1/2008 | Fildan ..................... A41C 3/04 450/36 |
| 2009/0265830 A1* | 10/2009 | Hendrickson ......... A41D 1/215 2/104 |
| 2010/0068971 A1* | 3/2010 | Hendrickson ........... A41C 3/04 450/31 |
| 2010/0159801 A1 | 6/2010 | Abbaszadeh |
| 2010/0159802 A1 | 6/2010 | Abbaszadeh |
| 2010/0261410 A1* | 10/2010 | Hirtz ....................... A41C 3/04 450/36 |
| 2013/0095727 A1 | 4/2013 | Abbaszadeh |
| 2014/0273737 A1* | 9/2014 | Cortese .................. A41D 1/205 450/31 |
| 2014/0364035 A1 | 12/2014 | Abbaszadeh |
| 2014/0364036 A1 | 12/2014 | Abbaszadeh |
| 2016/0015092 A1 | 1/2016 | Abbaszadeh |
| 2016/0150834 A1* | 6/2016 | Boele ................... A41C 3/0035 450/36 |
| 2016/0206007 A1 | 7/2016 | Op't Hof |
| 2016/0331045 A1 | 11/2016 | Cortese et al. |
| 2017/0273366 A1 | 9/2017 | Hoth |
| 2017/0280786 A1 | 10/2017 | Abbaszadeh |
| 2018/0000168 A1 | 1/2018 | Alva |
| 2018/0092408 A1 | 4/2018 | Hensel |
| 2018/0103691 A1 | 4/2018 | Alva |
| 2018/0132542 A1 | 5/2018 | Abbaszadeh |
| 2018/0206559 A1 | 7/2018 | Kosak |

\* cited by examiner

MULTI-LAYER NURSING GARMENT

CROSS REFERENCE TO RELATED APPLICATIONS

This application claims priority on U.S. Provisional Patent Application No. 62/383,457, entitled "Nursing Garment", filed on Sep. 4, 2016, which is incorporated by reference herein in its entirety and for all purposes.

STATEMENT REGARDING FEDERALLY SPONSORED RESEARCH OR DEVELOPMENT

This invention was not federally sponsored.

TECHNICAL FIELD

This invention generally relates to a nursing garment and more specifically to a Multi-layered Nursing Bra for comfortable and discrete breastfeeding.

BACKGROUND

Breastfeeding of a baby by a nursing woman has important benefits including nutrition, immunity to illnesses and psychological factors such as mother/baby bonding. Additional benefits of breastfeeding include (for the baby): breastmilk is easier for baby to digest and is "made to order" (breastmilk composition changes as baby ages and even throughout the day to meet growing baby's needs exactly), associated with increased 10, decreased risk of obesity, decreased risk of childhood illness and cancers (asthma, diabetes, heart disease, ear infections), decreased risk of SIDS, and increased bonding between mother and baby.

Proper support for mother and baby are necessary to ensure a successful breastfeeding relationship. Some common factors leading to early ending of breastfeeding include lack of support (by family, lactation consultants, or medical providers), latching issues (resulting in poor weight gain or destruction of mother's breast tissue further leading to pain and infection), difficulty establishing and maintaining a healthy breastmilk supply, and mother returning to work with minimal workplace support or provision for pumping of breastmilk. Without proper support, breastfeeding attempts are often unsuccessful in the long-term, leading to the breastfeeding relationship ending earlier than is decided by the mother-baby dyad.

Risks of not breastfeeding include (for the mother): increased risk of obesity, increased risk of blood pressure instability, return of menstrual cycle possibly leading to closely spaced pregnancy and lack of conservation of nutrients, increased rate of postpartum depression, increased sleep disturbances, increased risk of breast and ovarian cancer, increased risk of cardiovascular disease, increased risk of type 2 diabetes, increased risk of Rheumatoid arthritis, and osteoporosis. Additional negative effects of unsuccessful breastfeeding are: working mothers missing more work days due to increase in baby being sick, increased cost due to purchase of formula, and increase in health expenses due to decreased health.

These benefits and risks are well documented in scientific theory and literature. Thus, it is highly desirable to provide inventions that make it easier and more comfortable for a woman to breastfeed.

Many nursing garments are known in the prior art. However, the conventional problems with these garments are, when breastfeeding, the nursing women typically expose their breasts, which may make them uncomfortable if located in a public or crowded area.

In addition, the prior art nursing garments are difficult to wear or secure when worn. Further, opening or closing the breast cups of the nursing garments and other factors can be difficult, and a nursing woman is physically restricted in her ability to manage these factors while securing and maintaining the breast cups in place. Finally, the hooks or clasps for opening or closing are complex that opening and closing cups can be very difficult.

Further, in case of multi-layered or even a single layer of nursing garment, the cups and borders may fray or unravel in repeated wearing and laundering, thereby making it desirable to have a single nursing garment that does not have to be changed frequently.

Conventional solutions for covering exposed areas of the nursing women have several limitations and are often bulky, uncomfortable, unsafe, or difficult to handle.

In some conventional solutions, large towels or small sheets are used, which are bulky and typically made of heavy, non-breathable material. These are often too warm to wear, increasing the body temperature of the nursing women and the baby, resulting in difficult or uncomfortable breastfeeding. In addition, these "covers" need to be secured; otherwise a breastfeeding woman runs the risk over having her "cover" fall off.

Thus, there has existed a long-felt need for a multi-layered nursing garment made from a plurality of individual fabric layers which can all be made from the same fabric or which can be made from different but compatible fabrics. The ideal nursing garment should allow for the opening and closing the breast cups with additional options including soft fabric, suppleness, the ability to provide support and control, and with total elimination of edge stitching and/or the use of narrow bordering materials. A long-felt need has also existed for a nursing garment that will allow a woman to both breastfeed and/or pump either alternately or simultaneously from different breasts, without the woman having the change her clothes.

Therefore, the present invention aims by providing a nursing bra or other nursing garment with two breast cups of multilayer fabric, each of which can be opened for breastfeeding or pumping the milk from breasts with ease of opening or closing breast cups separately. The invention further provides a clasp mechanism having separate attachment points, so a nursing woman can peel off layer of the nursing garments as per her convenience. The invention also has a number of embodiments, including those where the clasp device is single and capable of accepting hooks from two or more layers, the use of two clasps where an outer layer hooks to one and an inner layer hooks to the second, the use of multiple clasps on different parts of the invention, and the use of multiple clips where one clip removably attached to the other.

SUMMARY

It is therefore an object of the invention to provide a multi-layered nursing garment, so that a nursing woman can peel off at least one layer for breastfeeding or pumping milk from the breasts.

Further, it is another object to provide a nursing garment that can help in selective breastfeeding such as opening one side of a breast cup at one time without removing the whole garment.

It is a primary object of the invention to provide a multi-layer nursing garment that allows a breastfeeding woman to both breastfeed and pump milk from either breast simultaneously using the same garment.

According to one aspect of the invention a multi-layered nursing garment includes breast support having a pair of breast cups, shoulder straps and a chest band that wraps around the torso provides breast cups that include at least two different layers; an inner layer and an outer layer are made of same or different fabric materials, which can be removably attached to the shoulder straps or bra cups of the nursing garment.

According to another aspect of the invention, each layer is attached on the shoulder straps by means of clasp, hook and clip arrangement, which are at least partially detachable from the shoulder straps.

According to another aspect of the invention clasps are configured with the shoulder straps for attaching the inner layer, said clasp includes a hook for attaching at least one layer.

According to another aspect of the invention a first clip is configured for attaching the inner layer.

According to another aspect of the invention a woman can "peel off" layers of her bra.

According to another aspect of the invention the outer layer is opened or closed by means of the first clip.

According to another aspect of the invention each layer is separately opened or closed to permit breastfeeding.

According to another aspect of the invention inner layer includes a slit through which permit breastfeeding or pumping the milk from the breast.

According to another aspect of the invention, a single clasp has the ability to accept a removable attachment from both inner layer and outer layer.

According to another aspect of the invention, a single clasp has the ability to accept a second clasp, such that the combination of clasps can accept a removable attachment from both inner layer and outer layer.

According to other aspect of the invention a multi-layered nursing garment consisting of breasts support having a pair of breast cups, shoulder straps and a chest band, said breast cups include an inner layer and an outer layer; a clasp is configured with the shoulder straps for attaching the inner layer, said clasp including a hook; a first clip is configured for attaching the outer layer with the hook arranged on the clasp of the shoulder straps, wherein, at least one layer of the breast cups is opened for breastfeeding or pumping the milk from the breast, and, at least one layer of the breast cups is opened to allow for the pumping of breast milk.

According to another aspect of the invention, a removable outer layer snaps or otherwise is removably attached to an inner layer.

According to another aspect of the invention, a removable outer layer and a removable inner layer are both snapped or otherwise removably attached to the bra cup or to the shoulder strap.

According to another aspect of the invention a multi-layered nursing garment includes breasts support having a pair of breast cups, shoulder straps and a chest band. Further, said breast cups include three layers, an inner layer, a middle layer and an outer layer where clasps are configured on the shoulder straps for attaching the inner layer. A first clip is configured for attaching the middle layer with a hook arranged on a first clasp of the shoulder straps and a second clip is configured for attaching the outer layer with the hook arranged on a second clasp of the shoulder straps. Further, a slit is formed on the middle layer for breastfeeding or pumping the milk from the breast.

According to another aspect of the invention, invention a multi-layered nursing garment includes breasts support having a pair of breast cups, shoulder straps and a chest band. Further, said breast cups include three layers, an inner layer, alternatively referred to as a "nursing sling", a middle layer and an outer layer where clasps are configured on the shoulder straps for attaching the inner layer. A first clip is configured for attaching the middle layer with a hook arranged on a first clasp of the shoulder straps and a second clip is configured for attaching the outer layer with the hook arranged on a second clasp of the shoulder straps. Further, a slit is formed on the middle layer for breastfeeding or pumping the milk from the breast. The nursing sling can be either "one half" or a full nursing sling.

There has thus been outlined, rather broadly, the more important features of the invention in order that the detailed description thereof may be better understood, and in order that the present contribution to the art may be better appreciated. There are additional features of the invention that will be described hereinafter and which will form the subject matter of the claims appended hereto. The features listed herein and other features, aspects and advantages of the present invention will become better understood with reference to the following description and appended claims. The accompanying drawings, which are incorporated in and constitute part of this specification, illustrate embodiments of the invention and, together with the description, serve to explain the principles of the invention.

It should be understood the while the preferred embodiments of the invention are described in some detail herein, the present disclosure is made by way of example only and that variations and changes thereto are possible without departing from the subject matter coming within the scope of the following claims, and a reasonable equivalency thereof, which claims I regard as my invention.

BRIEF DESCRIPTION OF THE DRAWINGS

This application will be described with reference to the following drawings. The drawings and the associated descriptions are provided to illustrate embodiments of the invention and not to limit the scope of the invention.

DETAILED DESCRIPTION

The term "clasped" is defined as connected or attached or closed, although not necessarily directly, and not necessarily mechanically. The term "unclasped" is defined as detached or opened. The term "clasp" refers generally to a device on the bra shoulder strap or bra cup that can receive a hook, button, or other means of removable attachment from the inner or outer layer. The term "nursing" is defined as breastfeeding. The terms "a" and "an" are defined as one or more unless this disclosure explicitly requires otherwise. The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs.

The present invention now will be described more fully hereinafter with reference to the accompanying drawings, in which some, but not all embodiments of the inventions are shown. While the following description details the preferred embodiments of the present invention is not limited in its application to the details of construction and arrangement of the parts illustrated in the accompanying drawings.

With reference to the figures, numerical designation has been given for each element to facilitate the reader's understanding of the present invention, and particularly with reference to the embodiments of the present invention illustrated in the figures; various preferred embodiments of the present invention are set forth below. The enclosed description and drawings are merely illustrative of preferred embodiments and represent several different ways of configuring the present invention. Although specific components, materials, configurations and uses of the present invention are illustrated and set forth in this disclosure, it should be understood that a number of variations to the components and to the configuration of those components described herein and in the accompanying figures can be made without changing the scope and function of the invention set forth herein.

Figure 1:
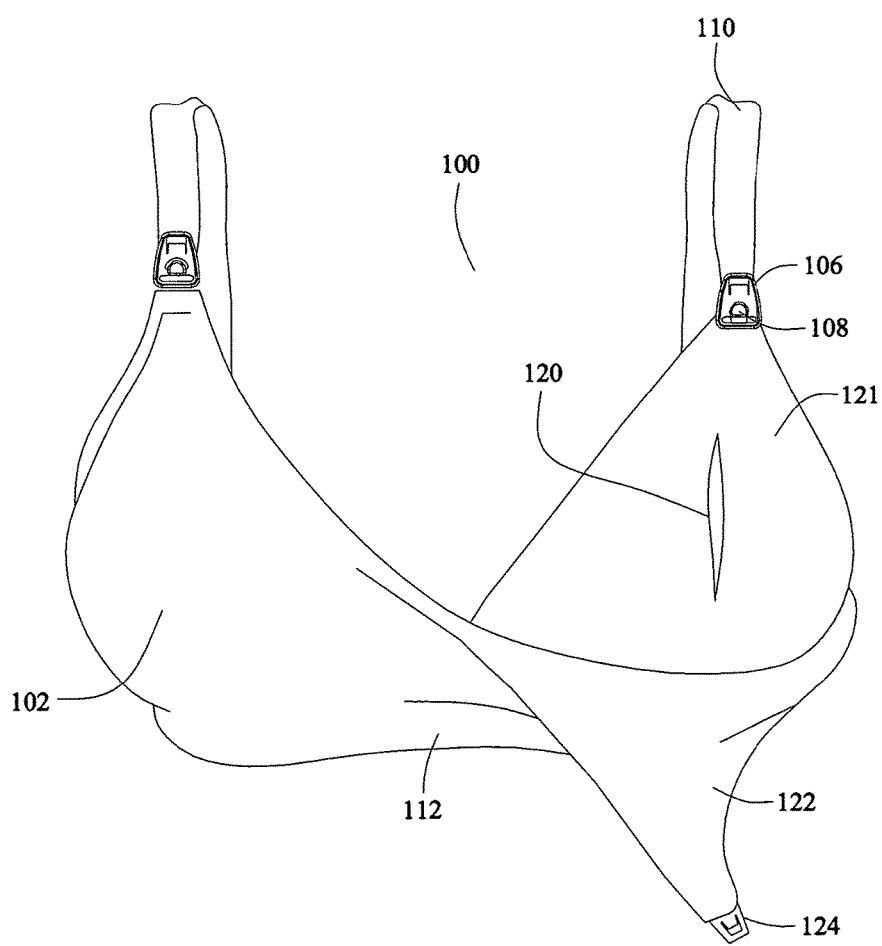
FIG. 1 is a perspective view of an exemplary multi-layered nursing garment in accordance with an embodiment of the present invention, with one outer layer pulled down.
Figure 2:
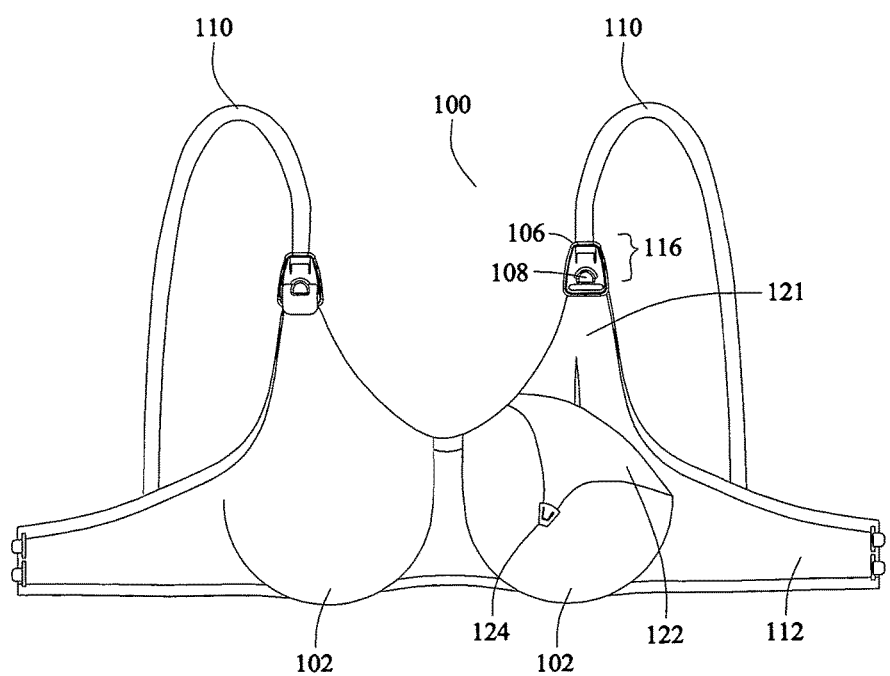
FIG. 2 is a perspective view of another exemplary multi-layered nursing garment in accordance with an embodiment of the present invention, with one outer layer partially pulled down.

Referring now to figures, in an exemplary embodiment of the present invention, a multi-layered nursing garment, generally referenced as 100, is shown. As shown in FIG. 1 and FIG. 2, the nursing garment, generally referenced as 100, is depicted as a brassiere or bra that permits a nursing woman to breastfeed/nurse a baby without removing the garment 100. However, it should be appreciated that the nursing garment 100 may be otherwise embodied. For example, in some embodiments, the nursing garment 100 may be embodied as a nursing bra but other items of nursing clothing are contemplated, including but not limited to nursing tops, nursing shirts, nursing dresses and any other item of clothing used for breastfeeding that includes the features described herein and/or is otherwise capable of performing the functions described herein. The nursing garment 100 includes breasts support having a pair of breast cups 102, shoulder straps 110 and a chest band 112 that wraps around the torso usually having hooks or fasteners at the back for fastening. The breast cups 102 that may be opened and closed to permit selective breastfeeding/nursing/milk pumping without removing the garment 100. That is, a nursing woman may wear the nursing garment 100 throughout the day and, when it is necessary to breastfeed to a baby, the breast cups 102 may be opened or unclasped to permit breastfeeding. By removing the need to frequently change her clothes, the breastfeeding woman is benefited both in terms of saving time, and in not subjecting said nursing garments to frequently washing and the inherent wear and tear that accompanies washing.

As shown in FIG. 1, and FIG. 2, according to an embodiment of the present invention, a multi-layered nursing garment with a pairs of breast cups 102, where the breast cups 102 are opened or closed by means of clasp, hook and clip arrangement as described herein, which are at least partially detachable from the shoulder straps 110. As shown in the FIG. 1 and FIG. 2, the breast cups 102 are multi-layered. In one exemplary embodiment, the breast cups 102 have at least two layers. However, in an alternate embodiment the number of the layers can be more and the invention is not limited to two layers. An inner layer 121 and an outer layer 122 are adhered to form the breast cups 102. In alternate embodiment, the layers may be also referred as first layer 121, second layer 122 and so on. Each layer, 121 and 122, can separately be opened or closed to permit breastfeeding or breast milk pumping, depending upon the requirements. However, in a preferred embodiment, outer layer 122 is opened or closed to permit breastfeeding. Further, each layer 121 and 122 can be made of same material or different garment fabric material without limiting the scope of the invention. As shown in the FIG. 1 and FIG. 2, the inner layer 121 includes a slit 120 to permit breastfeeding or pumping the milk from the breast.

In one embodiment, the shoulder strap 110 comprises of a clasp 106 and is configured to attach the inner most layer 121 of the breast cups 102 with the shoulder strap 110. Clasp 106 has a first hook 108 arrangement for attaching the outer layer 122 by a first clip 114. In another embodiment, the clip 114 may further comprises a slot (not shown in this Figure, but illustrated in FIG. 5A) for attaching another layer with the shoulder strap, where each layer is opened or closed by means of clip attached to the respective layer. In short, a major component of this invention is the ability to use one or more clips to sequentially open different layers of nursing garment, and to allow the nursing mother to select from breastfeeding and milk pumping as an option for either breast, and she can do so simultaneously with one breast being used for breastfeeding and the other for milk pumping if such is desirable.

In one embodiment, the breast cup 102 is partially detachable from the shoulder strap 104 by opening the layers 121 and 122 of the breast cups 102. In one preferred embodiment, a nursing woman can "peel off" layers of a bra as per her convenience.

In an exemplary embodiment, the layers 121 and 122 their attaching mechanism is illustrated for a breast cup as shown in the FIG. 1 and FIG. 2. However, this is merely for illustrative purpose without limiting scope of the present invention.

Figure 3:
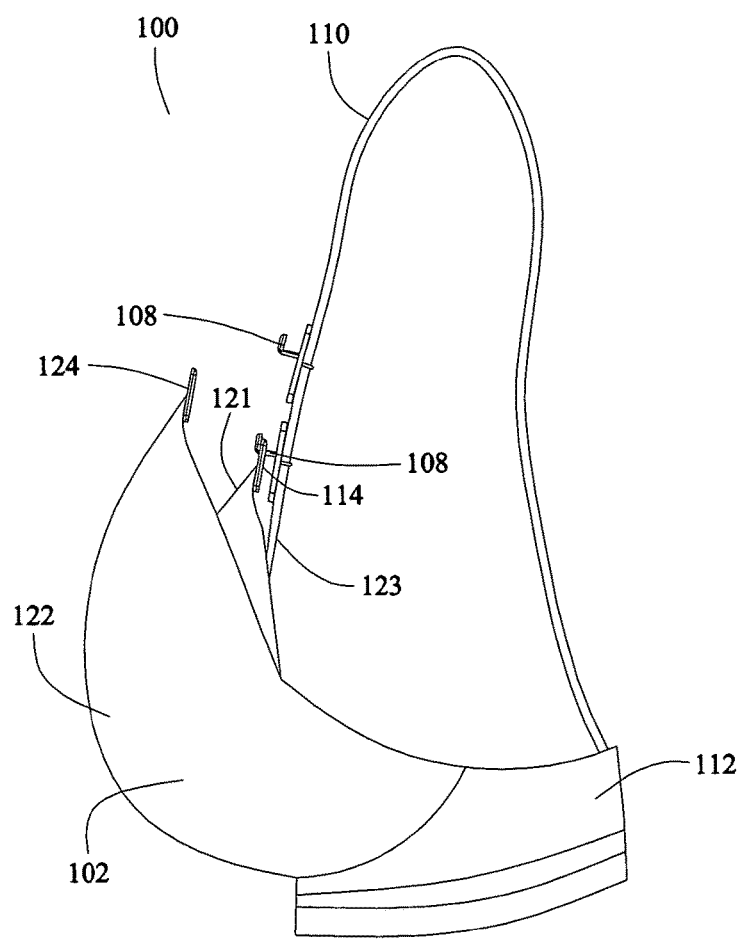
FIG. 3 illustrates a side view of a multi-layered nursing garment in accordance with another embodiment of the present invention, showing the means by which the various layers are detached on one embodiment of the invention.

In a preferred embodiment of the present invention is a multi-layered nursing garment 100 may comprise two or more different layers specifically for the breast cups 102. In another preferred embodiment, the inner layer may be attached to the shoulder strap by the clasp 106 as shown in FIG. 1, FIG. 2 and FIG. 3 and other layers that may be attached separately by the clip by layering on each other through a variety of means. In one of the preferred embodiment, a nursing woman can "peel off" layers of a bra as per her convenience such that she can peel off one or more layers to accomplish breast feeding and/or pumping the milk from the breast.

Figure 4:
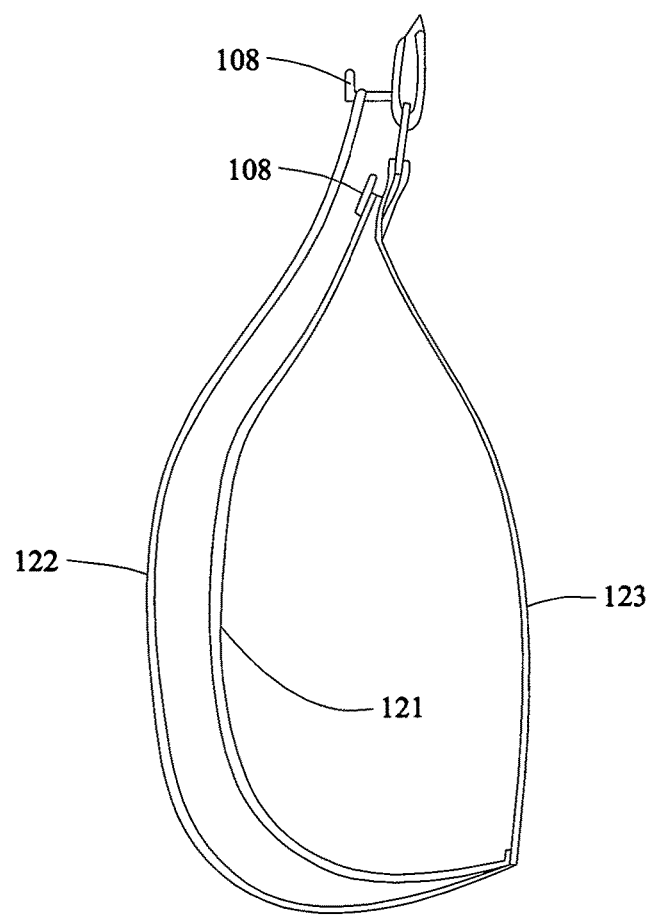
FIG. 4 illustrates a side view of the invention where the layers as they are attachment in accordance with another embodiment of the present invention.

As shown in FIG. 4, with some references numbers better viewed in FIG. 3, in another embodiment, the multi-layered nursing garment 100 may include three different layers, an inner layer 121, often called a "nursing sling", a middle layer 123 and an outer layer 122. In one exemplary embodiment, the breast cups 102 may comprises three different layers, an inner layer 121 (a nursing sling or a full third layer), a middle layer 123 and an outer layer 122. The inner layer 121 is configured to attach to the shoulder strap 110 with the clasp 106. Further, it is shown that the clasp 106 includes a first hook 108 for attaching the middle layer 123 by the first clip 114 and a second clasp 106 having hook 108 for attaching the outer layer by a second clip 116. The middle layer 123 has a slit 120 (as illustrated in FIG. 1) for pumping milk from the breast. It should be noted that the arrangement of two separate clasps 106 has advantages and disadvantages over other embodiment in the present invention.

In a preferred embodiment, the nursing garment 100 may comprise of more than two layers for example three different layers, where the innermost layer may or may not be a nursing sling—either half or full. In another preferred embodiment as shown in FIG. 3 and FIG. 4, the shoulder strap 110 is configured to attach the inner layer 121 of the breast cups 102 with the shoulder strap 110 and includes two clasps 106. Again, the clasps 106 additionally comprise hook 108 arrangement for attaching the middle layer 123 by a first clip 114 and a outer layer 122 by the second clasp 106. The first clip 114 is attached to middle layer 123 and the second clasp 106 is attached to outer layer 122, where the middle layer 123 or the outer layer 122 is opened or closed by means of the first clip 114 and the second clasp 106 attached to the respective layer.

In an alternate embodiment, the inner layer 121 is attached to the shoulder strap 110. Further, the hook 108 on the clasp 106 is configured to attach the outer layer 122 layer by the first clip 114 and the second clip 116 is configured to attach the middle layer 123 with the hook 108 on another clasp 106, where the middle layer 123 or the outer layer 122 is opened or closed by means of first clip 114 and second clip 116 attached to the respective layer. Further, as described above, the middle layer 123 includes the slit 120 for pumping milk from the breast.

A further embodiment provides a nursing garment with an outer layer, an inner layer, where the inner layer sits over a nursing sling, either half or full. In this embodiment, inner layer 123 can be attached to the shoulder strap 110, to the bra cup, or to clasp 106. Further, the hook 108 on the clasp 106 is configured to attach the outer layer 122 layer by the first clip 114 and the second clip 116 is configured to attach the inner layer 123 with the hook 108 on another clasp 106, or onto the same clasp, where the inner layer 123 and the outer layer 122 can be opened or closed by means of first clip 114 and second clip 116 attached to the respective layer. Further, as described above, the middle layer 123 includes the slit 120 for pumping milk from the breast.

Figure 5A:
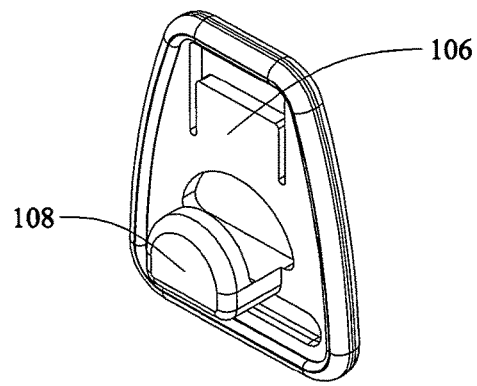
FIG. 5a is perspective view of the attachment mechanism of the multi-layered nursing garment clasp in accordance with an embodiment of the present invention.
Figure 5B:
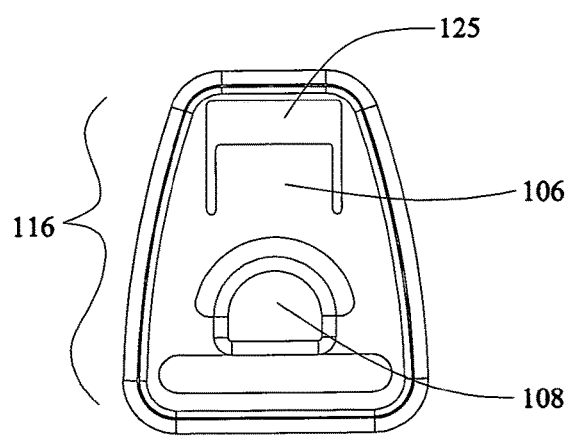
FIG. 5b is front view of the attachment mechanism of the multi-layered nursing garment clasp in accordance with an embodiment of the present invention.
Figure 5C:
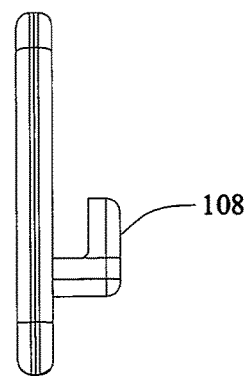
FIG. 5c is side view of the attachment mechanism of the multi-layered nursing garment clasp in accordance with an embodiment of the present invention.

As shown in FIG. 5a, FIG. 5b and FIG. 5c, the attachment mechanism is the clasp 106 is configured for clasping the inner layer 121 with the shoulder straps 110 or for unclasping from the shoulder straps 110. The clips 114 and 116 are configured for attaching the middle layer 123 and the outer layer 122 with the hook 108 on the clasp 106. Clasp 106 additionally comprises slot 124, to which one or more clips can be attached. In another preferred embodiment, clip 114 (from FIG. 4) removably attaches to slot 124, which clip 116 removably attaches to hook 108.

Further, the multi-layered nursing garment may include an electronic sensor on the breast cups 102 to indicate the status of a breast in the pair of breast cups and a computing device to record the sensor data indicative of whether the breast cup is open or closed. Further, the computing device records the sensor data, the sensor data is indicative amount of time each breast cup is open, thus start counting as breastfeeding time. For example, an electronic sensor (not shown in the figures) could measure the amount of time a woman breastfed or pumped milk from one breast or the other, and could also keep track of the amount of time that had elapsed between breastfeeding events.

Figure 6:
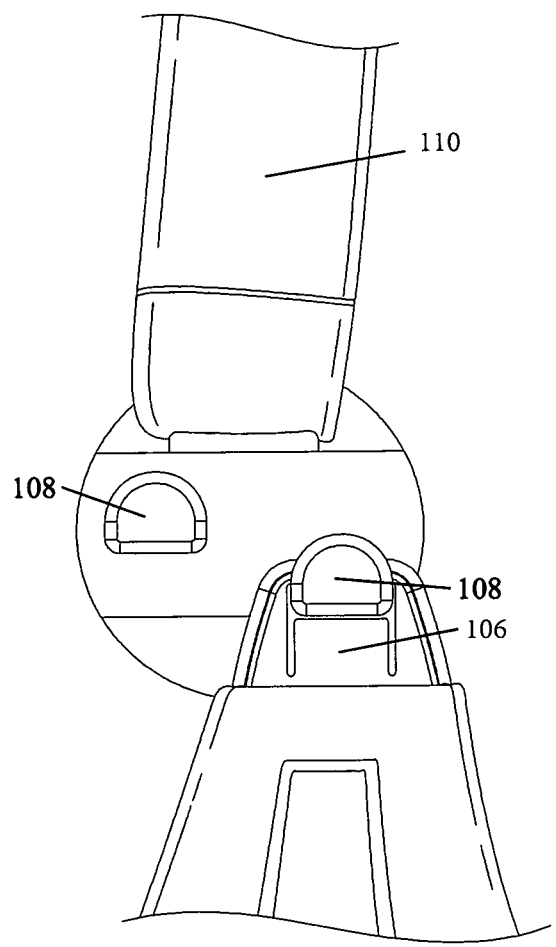
FIG. 6 is a front view of another embodiment of the invention where a single clasp has two sets of hooks.

FIG. 6 is a front view of another embodiment of the invention where a single clasp has two hooks 108. In this embodiment, two layers of the bra cup can attach to the same clasp through hooks. This is in contrast to other versions of the invention where a single clasp has both a slot and a hook.

Figure 7:
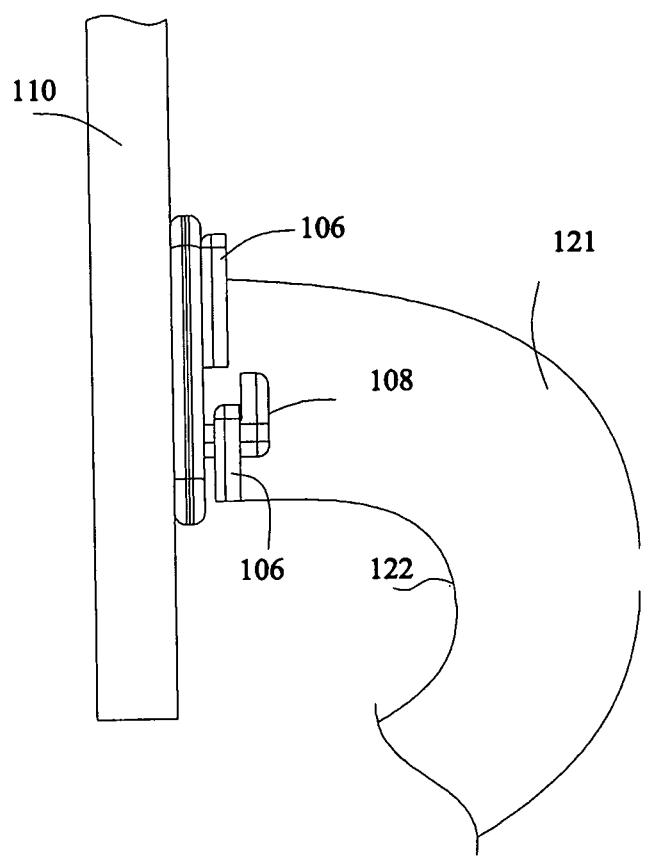
FIG. 7 is a side view of another embodiment of the invention.

As illustrated in FIG. 7, in another embodiment of the invention, a side view of the combination of a clasp and a nursing garment is shown. Clasp 106 is attached to bra strap 110. Clasp 106 has a slot (124 on FIG. 5A), into which second clip 116 removably attaches, thereby allow a user of the invention to pull back outer layer 122. Clasp 106 also has hook 108, over which first clip 114 hangs and attaches, thereby allowing a user of the invention to removably detach inner layer 123. By this method, a nursing mother could pump breast milk out of one breast and simultaneously breastfeed a baby with the other breast, all without have to change the nursing garment. This proves not only convenient for the nursing mother, but also saves on wear and tear of the nursing garment because there is not the necessity of changing clothes and washing the nursing garment so frequently.

Figure 8:
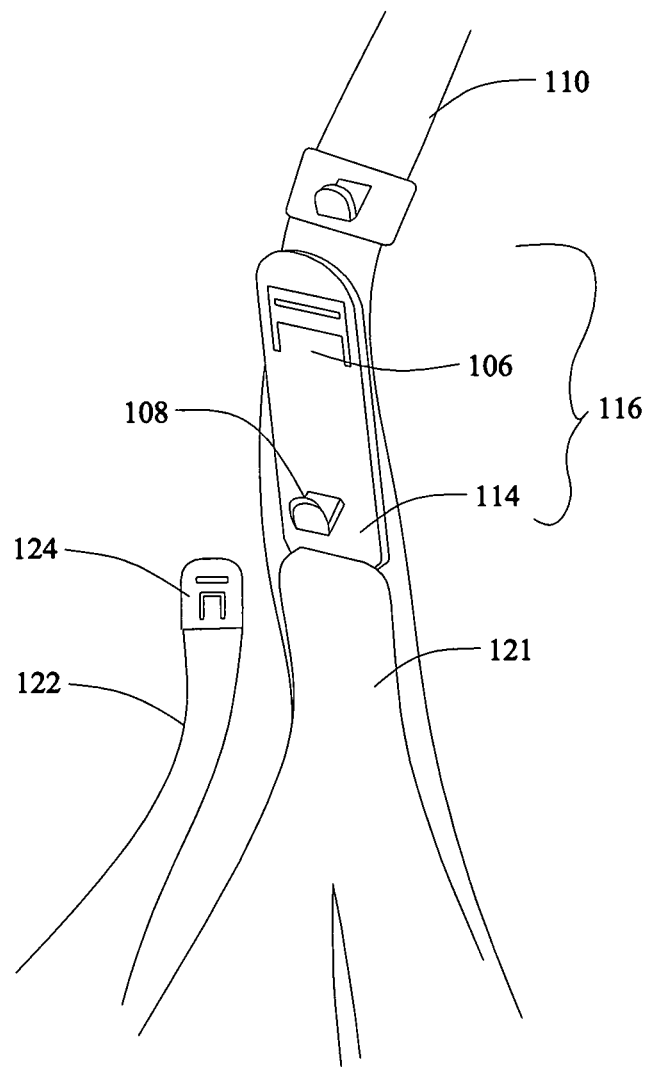
FIG. 8 is another view of the embodiment of the invention illustrated in FIG. 7.

FIG. 8 is a perspective view of the invention as displayed in FIG. 7. Clasp 106 is attached to shoulder strap 110. Clasp 106 has hook 108 disposed such that it can removably attach with second clip 116. Middle clip 114 is sewn to middle layer.

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

Certain features of the embodiments of the claimed subject matter have been illustrated as described herein; however, many modifications, substitutions, changes and equivalents will now occur to those skilled in the art. Additionally, while several functional blocks and relations between them have been described in detail, it is contemplated by those of skill in the art that several of the operations may be performed without the use of the others, or additional functions or relationships between functions may be established and still be in accordance with the claimed subject matter. It is, therefore, to be understood that the appended claims are intended to cover all such modifications and changes as fall within the true spirit of the embodiments of the claimed subject matter.

REFERENCE NUMBERS USED

100 Multi-layered nursing garment
102 Breast cups
106 Clasp

108 Hook
110 Shoulder straps
112 Chest band
114 First clip
116 Second clip
120 Slit
121 Inner layer
122 Outer layer
123 Middle layer

What is claimed is:

1. A multi-layered nursing garment, comprising:
a breast support having a pair of breast cups, shoulder straps and a chest band, where said breast cups include at least two different layers; including an inner layer and an outer layer;
a clasp, said clasp comprising a slot and a hook; the clasp located on a shoulder strap,
a first clip that is configured for attaching the outer layer with the slot, a second clip that is configured for attaching the inner layer to the hook, and
a slit on the inner layer,
wherein, the outer layer is removable for selective breastfeeding from the breast cups through the slit on the inner layer.

2. The multi-layered nursing garment of claim 1, wherein the outer layer and the inner layer are made of a same garment fabric material.

3. The multi-layered nursing garment of claim 1, wherein the the outer layer and the inner layer are made of two different garment fabric materials.

4. The multi-layered nursing garment of claim 1, wherein the clasp is located on each shoulder strap.

5. The multi-layered nursing garment of claim 1, where the breast cup comprises an outer surface and an inner surface, wherein the clasp is located on the outer surface of the breast cup.

6. The multi-layered nursing garment of claim 1, additionally comprising a second clasp, where the second clasp additionally comprises a second clasp hook, where the second clasp hook is located on the bra strap, above the clasp, and is configured to accept the first clip.

7. The multi-layered nursing garment of claim 1, additionally comprising a second clasp, where the second clasp additionally comprises a second clasp hook, where the second clasp hook is located on the bra cup, below the clasp, and is configured to accept the second clip.

8. A multi-layered nursing garment, consisting of:
a breast support having a pair of breast cups, shoulder straps and a chest band, where each of said breast cups include three layers, an inner layer, a middle layer and an outer layer;
each of said shoulder straps include a clasp including a hook for attaching the inner layer;
said middle layer including a first clip having a hook that is configured for attachment to a first clasp on each said shoulder strap,
said outer layer including a second clip including a hook configured for attaching said outer layer to a second clasp on each of the shoulder straps, and
a slit on the middle layer,
wherein, at least one layer of the breast cups is opened for breastfeeding or pumping a quantity of milk from the breast.

9. The multi-layered nursing garment of claim 8, where the inner layer is a nursing sling.

10. The multi-layered nursing garment of claim 9, wherein the outer layer and the inner layer are made of a same garment fabric material.

11. The multi-layered nursing garment of claim 9, wherein the clasps are located on the shoulder straps and are configured on the shoulder straps by attaching the inner layer.

12. The multi-layered nursing garment of claim 9, wherein the middle layer is opened or closed by the first clip and the outer layer is opened or closed by the second clip.

13. The multi-layered nursing garment of claim 12, wherein each layer is separately openable or closeable to permit breastfeeding.

14. The multi-layered nursing garment of claim 12, further including an electronic sensor, where the electronic sensor comprises a sending unit and a receiving unit, where the electronic sensor is configured with one of the sending unit and the receiving unit on the clasp and the other of the sending unit and the receiving unit on the clip, where the electronic sensor records the time and duration during which a bra cup is open.

15. The multi-layered nursing garment of claim 14, further includes a computing device that records an amount of breastfeeding time when the breast cup is open, such that the computing device starts operating when the breast cup is open, and stops operating when the breast cup is closed, such that a time period measured from when the computing device starts operating to when the computing device stops operating creates a measure of time that is start an amount of breastfeeding time.

16. A multi-layered nursing garment, comprising:
a breasts support having a pair of breast cups, shoulder straps and a chest band, where said breast cups include at least two different layers, including an inner layer and an outer layer;
a clasp is configured for attaching both of the two different layers, said clasp comprising two hooks;
a first clip is configured for attaching the outer layer with a first hook arranged on the clasp,
a second clip is configured for attaching the inner layer with a second hook arranged on the clasp, and
a slit on the inner layer,
wherein, the outer layer is removeable for selective breastfeeding from the breast cups through the slit on the inner layer.

17. The multi-layered nursing garment of claim 16, wherein the clasp is located on the shoulder strap.

18. The multi-layers nursing garment of claim 16, additionally comprising an electronic sensor, where the electronic sensor comprises a sending unit and a receiving unit, where the electronic sensor is configured with one of the sending unit and the receiving unit on the clasp and the other of the sending unit and the receiving unit on the clip, where the electronic sensor records a time and a duration during which a bra cup is open, additionally comprising a computing device that records an amount of breastfeeding time when the breast cup is open, such that the computing device starts operating when the breast cup is open, and stops operating when the breast cup is closed, such that a time period measured from when the computing device starts operating to when the computing device stops operating creates a measure of time that is an amount of breastfeeding time.

19. The multi-layered nursing garment of claim 16, wherein the clasp is located on the bra cup and additionally comprising an electronic sensor.

20. The multi-layered nursing garment of claim 19, where the electronic sensor additionally comprises a sending unit and a receiving unit, where the electronic sensor is configured with one of the sending unit and the receiving unit on the clasp and the other of the sending unit and the receiving unit on the clip, where the electronic sensor records the time and duration during which a bra cup is open, additionally comprising a computing device that records amount of time when the breast cup is open, thus start counting as breastfeeding time.

* * * * *